United States Patent
Bernhardt et al.

(10) Patent No.: US 11,185,296 B2
(45) Date of Patent: Nov. 30, 2021

(54) METHOD FOR THE CREATION OF X-RAY IMAGES, AND X-RAY SYSTEM

(71) Applicant: Siemens Healthcare GmbH, Erlangen (DE)

(72) Inventors: Philipp Bernhardt, Forchheim (DE); Michael Stark, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 281 days.

(21) Appl. No.: 16/345,629

(22) PCT Filed: Oct. 9, 2017

(86) PCT No.: PCT/EP2017/075649
§ 371 (c)(1),
(2) Date: Jul. 26, 2019

(87) PCT Pub. No.: WO2018/077603
PCT Pub. Date: May 3, 2018

(65) Prior Publication Data
US 2020/0022662 A1 Jan. 23, 2020

(30) Foreign Application Priority Data
Oct. 27, 2016 (DE) .................. 10 2016 221 205.2

(51) Int. Cl.
*A61B 6/06* (2006.01)
*A61B 6/02* (2006.01)
(Continued)

(52) U.S. Cl.
CPC .............. *A61B 6/06* (2013.01); *A61B 6/027* (2013.01); *A61B 6/4291* (2013.01);
(Continued)

(58) Field of Classification Search
CPC ......... A61B 6/027; A61B 6/06; A61B 6/4233; A61B 6/4291; A61B 6/5205; A61B 6/5258; G01N 23/04; G01N 23/20; G01T 1/2019
See application file for complete search history.

(56) References Cited

U.S. PATENT DOCUMENTS

| 4,315,146 A | 2/1982 | Rudin |
| 4,644,575 A | 2/1987 | Kruger |

(Continued)

FOREIGN PATENT DOCUMENTS

| DE | 3619027 A1 | 12/1986 |
| DE | 19509021 A1 | 9/1996 |

(Continued)

OTHER PUBLICATIONS

German Office Action for German Application No. 10 2016 221 205.2 dated Oct. 17, 2017.
(Continued)

*Primary Examiner* — Mark R Gaworecki
(74) *Attorney, Agent, or Firm* — Lempia Summerfield Katz LLC (57) ABSTRACT

The invention relates to a method (62, 64) for creating x-ray images as well as to an x-ray system. During the creation of an x-ray image, a slit diaphragm (16) is moved in front of an object (24) to be x-rayed, along a path extending between a radiation source (10) and said object (24), in order for the object (24) to be scanned. X-rays emitted by the radiation source (10) are detected by a detector (20) upon penetration of the slit diaphragm (16) and the object (24) to be x-rayed. In order to create an x-ray image using a simplified slot scanning technique, the x-ray image is created without the need for a second slit diaphragm (16) between the object (24) to be x-rayed and the detector (20), and only the radiation of which the intensity (60), detected by the detector (Continued)

(20) during the scan, exceeds a predefined threshold value is processed.

13 Claims, 4 Drawing Sheets

(51) Int. Cl.
    *G01T 1/20*     (2006.01)
    *A61B 6/00*     (2006.01)
    *G01N 23/04*     (2018.01)
    *G01N 23/20*     (2018.01)

(52) U.S. Cl.
    CPC .......... *G01T 1/2018* (2013.01); *A61B 6/4233* (2013.01); *A61B 6/588* (2013.01); *G01N 23/04* (2013.01); *G01N 23/20* (2013.01)

(56) References Cited

U.S. PATENT DOCUMENTS

| | | |
|---|---|---|
| 4,646,339 A | 2/1987 | Rice |
| 4,916,723 A | 4/1990 | Geluk |
| 2006/0104415 A1 | 5/2006 | Unger |
| 2010/0278299 A1* | 11/2010 | Loustauneau .......... A61B 6/587 378/13 |

FOREIGN PATENT DOCUMENTS

| | | |
|---|---|---|
| DE | 102005054824 A1 | 5/2006 |
| DE | 102013215042 A1 | 2/2015 |
| EP | 0251407 A1 | 1/1988 |

OTHER PUBLICATIONS

Liu, Xinming, et al. "An alternate line erasure and readout (ALER) method for implementing slot-scan imaging technique with a flat-panel detector-initial experiences." IEEE transactions on medical imaging 25.4 (2006): 496-502.

PCT International Search Report and Written Opinion of International Searching Authority dated Jul. 17, 2018, corresponding to PCT International Application No. PCT/EP2017/075649.

PCT Preliminary Opinion as an Annex to the Result the Participator dated Mar. 28, 2018, for corresponding PCT/EP2017/075649.

* cited by examiner

METHOD FOR THE CREATION OF X-RAY IMAGES, AND X-RAY SYSTEM

This application is the National Stage of International Application No. PCT/EP2017/075649, filed Oct. 9, 2017, which claims the benefit of German Patent Application No. 10 2016 221 205.2, filed Oct. 27, 2016. The entire contents of these documents are hereby incorporated herein by reference.

BACKGROUND

The present embodiments relate to generating x-ray images.

In x-ray-based imaging devices known from the prior art, a basic construction including a punctiform x-ray source and a collimator is typically provided. X-ray radiation is emitted in a radial direction from the x-ray source (e.g., an x-ray tube). The x-ray radiation is channeled through a collimator into an irradiation volume. The x-ray radiation at least partially penetrates an object to be x-rayed, which, from a viewpoint of the x-ray source, is arranged on the other side of the collimator and is detected or registered with the aid of an x-ray detector. The x-ray detector may be embodied as a film or as a flat panel detector, for example. Alternatively or additionally, the x-ray detector may include an image intensifier. According to the current state of the art, there are three possibilities for reducing scattered radiation (e.g., that arising in the object to be x-rayed, which otherwise impinges in an undirected manner on the detector). This scattered radiation is unwanted in this situation since the scattered radiation contains no usable image information at all about the object to be x-rayed and adds image noise to the x-ray image, resulting in a degradation in overall image quality and specifically in a reduction in contrast. This loss in image quality may be compensated for by a higher radiation dose, though this may lead to negative effects (e.g., when the object to be x-rayed is a patient or biological tissue). Antiscatter grids, an airgap technique, or a slot-scan technique are currently used to reduce the scattered radiation.

In the slot-scan technique, according to the current state of the art, two slit diaphragms are provided. The two slit diaphragms are moved in parallel at a constant speed, one in front of the patient and the other behind the patient. The smaller an irradiated subregion of the patient is, the smaller is the scattered radiation component of the total radiation reaching the detector, since a proportionately greater percentage of the scattered radiation then does not impinge on the detector but is incident on the second slit diaphragm. A movement of the slit diaphragms or of a bundle of rays passing through the first slit diaphragm across the patient or across the designated region to be radiographed is referred to as a scan. Following a scan, a complete x-ray image is present. A disadvantageous aspect here is that a severe loading of the x-ray tube assembly or x-ray source results because very much more power is demanded of the x-ray tube assembly or x-ray source than in the case of an x-ray image acquisition or scan without slit diaphragms. A likewise disadvantageous aspect is the particularly complex and error-prone mechanical guidance of the two slit diaphragms, which requires precise coordination.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for generating x-ray images using a simplified slot-scan technique and a corresponding x-ray system are provided.

The method according to one or more of the present embodiments for generating x-ray images provides that in the course of generating an x-ray image, a slit diaphragm is moved in front of an object to be x-rayed along a path extending between a radiation source and the object to be x-rayed for the purpose of scanning the object to be x-rayed. In the process, radiation emitted by the radiation source is detected by a detector after the radiation has passed through the slit diaphragm and the object to be x-rayed. Examples of the object to be x-rayed may include a physical object, a patient, or also a subregion of such. In order to generate the x-ray image using a simplified slot-scan technique, it is provided according to one or more of the present embodiments that the x-ray image is generated without the use of a second slit diaphragm arranged between the object to be x-rayed and the detector and in the process only such radiation is evaluated with an intensity detected during the scan by the detector that is greater than a predefined threshold value. In other words, therefore, the second slit diaphragm provided in known prior art methods is omitted, and this omission is compensated for by a correspondingly adapted thresholding method. In one embodiment, the predefined threshold value may be chosen or set such that typical intensities of unwanted scattered radiation lie below the threshold value. In this way, a proportion of the scattered radiation in the total radiation used for the definitive x-ray image is thus reduced to a minimum. It may also be provided to take into account, in addition to the threshold value, known information with respect to a geometry of a radiation field of the radiation emitted by the radiation source. The information may be determined, for example, from a shape of a slit and a motion time of the slit diaphragm. This approach may be used, for example, for generating a mask or reference x-ray image and/or may be necessary or advantageous, for example, in the case of relatively low or small radiation doses, since particularly good image quality may be achieved by this. In one embodiment, use is henceforth made only of a slit diaphragm that is to be moved mechanically. As a result of this, component requirements, cost overheads, and vulnerability to failure may be reduced, and at the same time, reliability, durability, and ease of use of a corresponding x-ray system or x-ray device may be improved.

Typically, a beam cone or radiation field of the radiation emitted by the radiation source (e.g., the x-ray radiation) is significantly expanded or widened after passing through the object to be x-rayed, with the result that in the prior art, it was necessary to configure the second slit diaphragm with a correspondingly large surface area. By omitting the second slit diaphragm, it is therefore possible also to achieve weight and material savings and to configure a guidance mechanism for guiding the first slit diaphragm in a simplified or more compact design. With the present method, there is also no need to coordinate two mechanical diaphragms with one another, to align the two mechanical diaphragms to one another, and to synchronize the two mechanical diaphragms in movements. There is also no requirement for a more powerful radiation source in comparison with known prior art methods.

In a further embodiment of the method, in the course of the generation of an x-ray image, a plurality of constituent image datasets are read out from the detector during the scan. In other words, two or more constituent image datasets are read out. The x-ray image is then assembled from all subdomains of the constituent image datasets in which the detected intensity is greater than the predefined threshold value. In other words, the scan is therefore provided for generating or obtaining a single definitive x-ray image. Effectively, however, a plurality (e.g., two or more) partial images or partial x-ray images are acquired during the one scan. The partial images in each case do not reproduce or represent the complete object to be x-rayed. Such a partial image corresponds to a constituent image dataset. The subdomains of the constituent image datasets in which an intensity or brightness value lies below the threshold value correspond to the areas of the detector that have not been illuminated or exposed or have been illuminated or exposed only by scattered radiation. In this case, the threshold value used may also be dynamically adjusted, changed, or varied (e.g., during the scan). The threshold value may be obtained as a percentile of a histogram, for example. By this, it is possible, for example, to avoid the risk that an incorrect, imprecise, or suboptimal mask image will be generated. The constituent image datasets acquired and read out during the scan are buffered until the scan has been terminated and subsequently are used to calculate or assemble the x-ray image as a complete image. For that purpose, only respective intensity or radiation maxima or corresponding maximum domains of the constituent image datasets may be used, for example, and combined to form the definitive or final x-ray image. It is also possible that the respective unilluminated subdomains, or subdomains illuminated only by scattered radiation, of each constituent image dataset are immediately discarded after the respective constituent image dataset has been read out, thereby enabling an unnecessary buffering of the corresponding data to be dispensed with. When the x-ray image is composed, an averaging of definitely overlapping areas, acquired image data, or acquisition domains of the constituent image datasets may be provided. A mean sliding over time (e.g., moving average) may, for example, be used or applied in such an averaging operation.

It may be possible to coordinate the readout of the constituent image datasets or a corresponding readout rate with the movement of the slit diaphragm such that the respective subdomains of all constituent image datasets subsequently used for the x-ray image precisely adjoin or border seamlessly on one another. Alternatively, however, it may also be possible that the subdomains of in each case at least two constituent image datasets acquired or read out in immediate succession overlap one another. In this case, it is necessary to take the overlap into account when the final x-ray image is assembled. This may happen, for example, in that no addition of the intensities or brightness values of the constituent image datasets is carried out in the areas of overlap. Instead, for example, an average value that then serves as an intensity or brightness value for the final x-ray image at the point of overlap may be formed.

A detector or image receiver that allows, supports, or offers a sufficiently high readout rate or image readout rate is used. In a further embodiment of, the constituent image datasets are read out from the detector at a rate of at least 60 Hz. Sixty complete constituent image datasets may be read out in one second. For practical applications, a scan lasts, for example, 100 ms, and/or successive scans are performed or started at a frequency of 10 Hz. However, both the scan duration and the acquisition frequency of the x-ray images may also be chosen differently. Depending on application case or application field of the x-ray images or x-ray image acquisitions, image acquisition frequencies of the x-ray images of between 3 Hz and 30 Hz may be provided, for example. Using an image readout rate of at least 60 Hz, multiple constituent image datasets may be acquired during each scan.

In a further embodiment, the detector has an active pixel sensor, and the radiation detected by the sensor during the scan by the detector is ignored or discarded in a pixel-precise manner as long as the respective intensity of the x-ray radiation impinging on the pixel is less than the predefined threshold value. As long as the respective intensity is greater than the threshold value, the radiation or radiation intensity detected by the active pixel sensor during the scan is integrated in a pixel-precise manner. In this case, the threshold value is individually and/or dynamically adjustable for each x-ray image and/or is adjusted or set or specified dynamically. For the pixel-precise evaluation, a dedicated amplifier circuit may be assigned to each pixel, or each picture element of the detector, or each picture element of the detector may include or have a dedicated amplifier circuit. For example, when the detector is manufactured using semiconductor or CMOS technology, further functions may also be integrated into the detector itself. For example, a respective circuit for exposure control, for contrast correction, and/or for analog-to-digital conversion may be provided. When an active pixel sensor is used, corresponding electronics may directly read out a voltage signal of any individual pixel without the need initially to shift or forward corresponding electrical charges.

If the threshold value is predefined such that an intensity or illumination of a respective pixel caused only by unwanted scattered radiation lies or remains below the threshold value, then it is possible for the detector to forward or read out, in a selective and automated manner without further data processing overhead, only such data that contains actual data or information to be utilized for the final x-ray image. Data to be utilized in this case may include such data carrying image information about the object to be x-rayed or image information describing or characterizing the object to be x-rayed.

In a further embodiment, the radiation source is operated in a pulsed mode at a duty cycle of at least 50 (e.g., of at least 90%). Since very small duty cycles of mostly 10% are employed in prior art x-ray image acquisition methods, the radiation sources or x-ray tube assemblies used there are substantially limited by peak load or peak performance capability and not by continuous load or continuous performance capability. With the increase in duty cycle provided by one or more of the present embodiments, typical known x-ray radiation sources may marshal significantly more capacity for an x-ray image, since the x-ray radiation sources have power reserves with respect to continuous load still unused in the prior art methods. A dose per x-ray pulse may be significantly increased with at least virtually the same peak power, since the radiation source (e.g., an x-ray tube) may be operated at a continuous load limit or at maximum continuous load, and the maximum continuous power is applied during a greater or longer duty cycle.

Since the slit diaphragm is guided along in front of the object to be x-rayed during the scan in the present method, a local exposure time of a subregion of the object to be x-rayed remains unchanged compared with conventional slot-scan techniques. In sufficiently small environments, the x-ray images therefore exhibit no additional lack of definition as a result of possible movements of the object to be x-rayed. In the case of extensive movements of the object to be x-rayed during the scan, such as in the case of an involuntary movement of a patient, for example, the corresponding final x-ray image is likewise not lacking in definition, but simply compressed or stretched according to the movement. In this case, the duration of the scan may be coordinated or synchronized with the pulse length of a radiation pulse emitted by the radiation source so that, for example, the scan duration may correspond to the pulse duration or pulse length. This allows optimal use to be made of the available radiation capacity in order to achieve the best possible image quality.

In a further embodiment, the radiation source is operated continuously during the immediately following generation of multiple x-ray images. In other words, a radiation source intended only for a continuous mode of operation or a radiation source that may also be used in a pulsed mode of operation and is operated at a duty cycle of 100% may be provided or used in this case. The scan duration may then be optimally adjusted to the respective demands or requirements without the risk that a subregion of the object to be x-rayed will be scanned with the aperture of the slit diaphragm while the radiation source emits no power (e.g., no x-ray radiation). In other words, the scan duration may therefore correspond to a period of time between two successive pulses, pulse starts, or pulse start times in a conventional pulsed mode of operation of the radiation source. In this fixed time interval, the radiation source may therefore deliver more energy, thus resulting in a higher level of performance overall.

In a further embodiment, the slit diaphragm is rotatably mounted and during the scan, is rotated around an axis of rotation that extends, for example, at least approximately parallel to a central ray of a bundle of rays emitted by the radiation source. In other words, the slit diaphragm is therefore rotated or turned in order to move a slit or an aperture of the diaphragm along the object to be x-rayed. Using an arrangement of the type, it is possible to improve a mechanical stability of the diaphragm arrangement or of the corresponding x-ray system or x-ray device, to simplify a precise mechanical guidance of the aperture or slit along the object to be x-rayed, and to minimize a mechanical load and a vulnerability to failure. In one embodiment, the slit diaphragm may be realized as rotationally symmetrical (e.g., in the form of a wheel or circular disk). A continuously pivotable or rotatable mounting enables a mechanically simple and precise movement of the slit diaphragm. A simple and precise adjustment of the movement of the slit along the object to be x-rayed is possible by a corresponding control of the speed of rotation or revolution.

An x-ray system according to one or more of the present embodiments includes a radiation source (e.g., an x-ray radiation source), a movably mounted slit diaphragm, a detector by which radiation emitted by the radiation source is detectable, and a data processing device (e.g., a data processor) that is configured for carrying out at least one embodiment of the method.

In a further embodiment of the x-ray system, the slit diaphragm is embodied as a disk or circular disk that is mounted as rotatable around an axis of rotation or central axis and has at least one (e.g., more than one) slit extending in the radial direction. In this arrangement, the slit or slits may extend through the disk in each case either completely or only in a segment or subsection in the radial direction from the centrally arranged axis of rotation to an edge of the disk. In one embodiment, when multiple slits or apertures are used, these may be arranged symmetrically and/or be of equal size and/or of the same shape or design. This enables a consistent acquisition of successive x-ray images with minimum synchronization overhead and may also enable a particularly small movement of the slit diaphragm that consequently involves little mechanical load or complexity. Different slits may be used, for example, in an acquisition or generation of a series of multiple x-ray images for two successive scans or x-ray images. As a result of this, the speed of rotation of the slit diaphragm may be chosen lower than would be possible with the rotational speed where only one slit is used.

In a further embodiment of the x-ray system, each slit of the disk has a greater extension in the radial direction than in a circumferential direction of the disk. Respective subsections of the slit diaphragm delimiting the slits from one another and impermeable to the radiation emitted by the radiation source may have a greater extension or elongation in the circumferential direction than the slits. By this, even in the case of a plurality of slits, no unwanted overlay, scatter, interaction, and/or interference effects occur between the individual slits and/or between bundles of rays passing through different slits. Radiation may also be irradiated or emitted through multiple slits simultaneously. The object to be x-rayed may then be irradiated, x-rayed, or scanned, for example, simultaneously in different subregions.

Multiple slits of the slit diaphragm, insofar as the slits are provided in or on the slit diaphragm, may be illuminated or irradiated simultaneously by the radiation emitted by the radiation source.

The functional embodiments of the method and of the x-ray system described hitherto and in the following, as well as in the claims, as well as the corresponding advantages, are in each case transferable in both directions between the method and the x-ray system. This applies also to components, devices, and equipment used or usable for carrying out the method.

DETAILED DESCRIPTION

Figure 1:
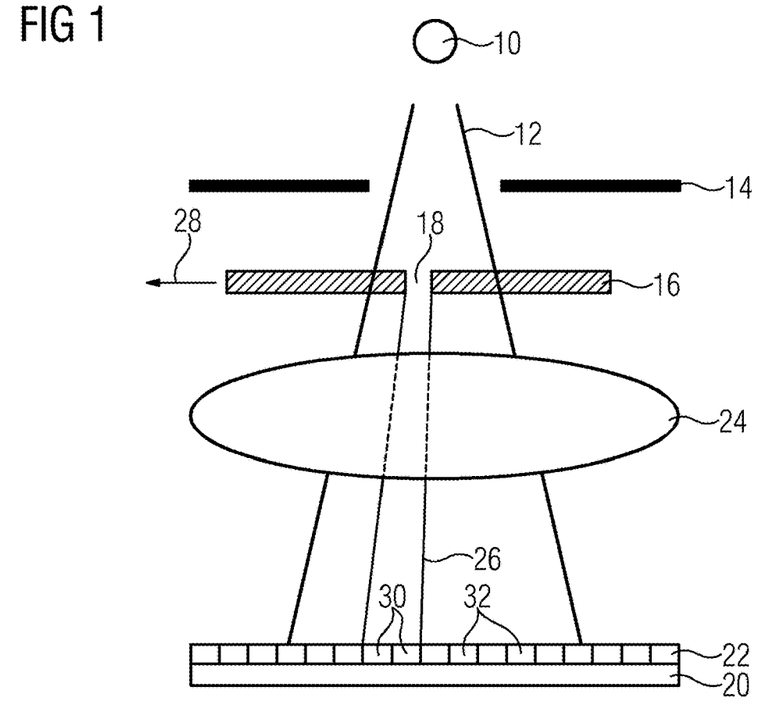
FIG. 1 shows a schematic and partial sectional view of one embodiment of an x-ray system having a single slit diaphragm.

FIG. 1 shows a partial and schematic sectional view of one embodiment of an x-ray system. In the present example, the x-ray system includes a radiation source 10 that emits x-ray radiation in a beam cone 12. The radiation source 10 may also emit radiation in other directions. A collimator 14 includes an aperture that allows through or channels at least a portion of the x-ray radiation emitted by the radiation source 10. In the present example, the beam cone 12 passes through the aperture of the collimator 14 and then impinges on a slit diaphragm 16. In contrast to the arrangement illustrated here (e.g., irrespective of other embodiments of the x-ray system illustrated or described), the slit diaphragm 16 may alternatively be arranged between the radiation source 10 and the collimator 14. In such an arrangement, the slit diaphragm 16 may be arranged particularly close to the radiation source 10. As a result, the beam cone 12 or a corresponding radiation field is then still particularly small when impinging on the slit diaphragm. The slit diaphragm 16 has, as an aperture, at least one slit 18 through which a portion of the radiation of the beam cone 12 passes. Thus, in the drawing plane shown, transversely to the propagation direction of the x-ray radiation of the beam cone 12, the slit 18 has a smaller breadth or width than the beam cone 12 at the level of the slit diaphragm 16. Consequently, a portion of the x-ray radiation of the beam cone 12 impinges on impermeable sections of the slit diaphragm 16, while another portion of the x-ray radiation passes through the slit 18 and hence through the slit diaphragm 16. The slit diaphragm 16 may be arranged, for example, at a distance of 20 cm from the radiation source 10 or from the collimator 14.

On a side of the slit diaphragm 16 facing away from the radiation source 10, there is arranged, in the present example, a detector 20 that has, on a side facing toward the slit diaphragm 16, an arrangement of pixels 22 for detecting x-ray radiation impinging thereon. Arranged between the slit diaphragm 16 and the detector 20, in the present example, is a schematically represented patient 24, of whom at least a subregion represents an object to be x-rayed that is to be radiographed by the x-ray radiation and imaged by the detector 20. During the radiographic procedure, regions of the patient 24 are penetrated by a bundle of rays 26 consisting of x-ray radiation emitted by the radiation source 10 and passing through the slit 18 of the slit diaphragm 16.

The slit diaphragm 16 is movably mounted and is able, in the present example, to be moved, as indicated here by an arrow 28, in a direction or plane that extends at right angles to a notional line connecting the radiation source 10 to the detector 20. By a movement of the slit diaphragm 16, it is therefore possible to move the slit 18 through the bundle of rays 12 and in this way, at least partially scan the patient 24 or the object to be x-rayed. In such a scan, the slit diaphragm 16 is moved such that the bundle of rays 26 passes or is radiated once through the maximum subregion of the patient 24 treatable by radiation (e.g., the subregion lying within the beam cone 12 and in this case therefore representing the object to be x-rayed), in the movement direction of the slit diaphragm 16. At the time instant represented in the present example, the bundle of rays 26, after having passed through the patient 24, impinges on illuminated pixels 30 of the detector 20. At the time instant shown, the remaining or other pixels of the pixels 22 are not illuminated by the bundle of rays 26 and therefore represent dark pixels 32.

After passing through the patient 24, the x-ray radiation of the bundle of rays 26 carries image information about the radiographed subregion of the patient 24. The image information is ultimately to be visualized in an x-ray image. However, when the x-ray radiation passes through the patient 24, scattered radiation is also produced. The scattered radiation is undirected and contains or carries no usable image information at all. The x-ray radiation of the bundle of rays 26 carrying image information is also referred to as primary radiation and, together with the scattered radiation exiting the patient 24 in the direction of the detector 20, forms a total sum of radiation impinging on the detector 20 (e.g., on the pixels 22). This therefore provides that the illuminated pixels 30 are illuminated by primary radiation, while the dark pixels 32 are not illuminated or are illuminated only by scattered radiation. With the movement of the slit diaphragm 16, there is also a change in which of the pixels 22 are the illuminated pixels 30 in each case.

Figure 2:
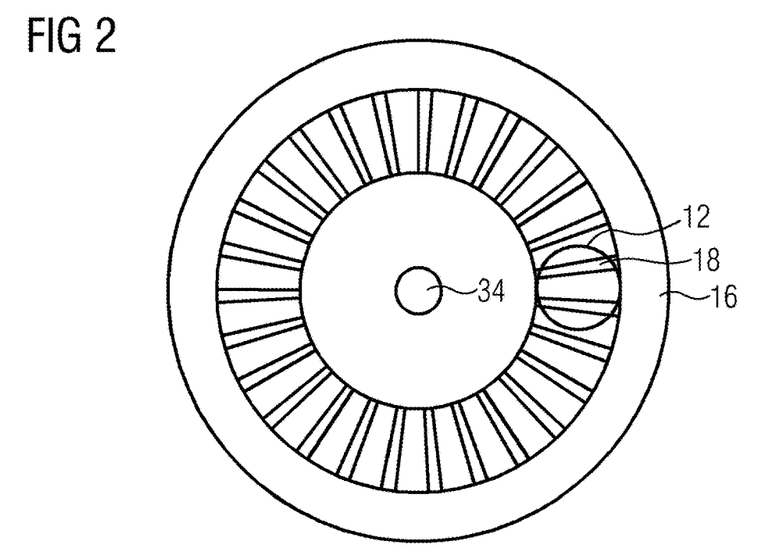
FIG. 2 shows a schematic plan view onto an exemplary rotatable slit diaphragm.

FIG. 2 shows a schematic plan view of the slit diaphragm 16, which in the present example, is embodied as a rotationally symmetrical disk or circular disk or as a wheel, and has an axis of rotation 34 at a midpoint or center. The slit diaphragm 16 may therefore be continuously rotated around the axis of rotation 34, in which case, therefore, no changes of direction or reversals of the direction of movement or rotation are to occur. As a result, a mechanical loading of the slit diaphragm 16 and of a drive is reduced compared to a conventional mechanical diaphragm guide intended for linear movements. The axis of rotation 34 may extend at right angles to the direction of movement or rotation of the slit diaphragm 16 indicated by the arrow 28 and is then therefore arranged, at least approximately, parallel to a central ray of the beam cone 12. In the present example, the slit diaphragm 16 has a plurality of slits 18, the respective main extension direction of which runs in the radial direction of the slit diaphragm 16. In the circumferential direction of the slit diaphragm 16, the slits 18 may have an average extension or aperture width of 1 mm, for example, while the nontransparent areas of the slit diaphragm 16 arranged in each case between two of the slits 18 may have an average extension in the circumferential direction of, for example, 5 mm. For illustration purposes, the beam cone 12 is also indicated here, which, as shown by way of example, can therefore also illuminate or cover a plurality of the slits 18 simultaneously.

Figure 3:
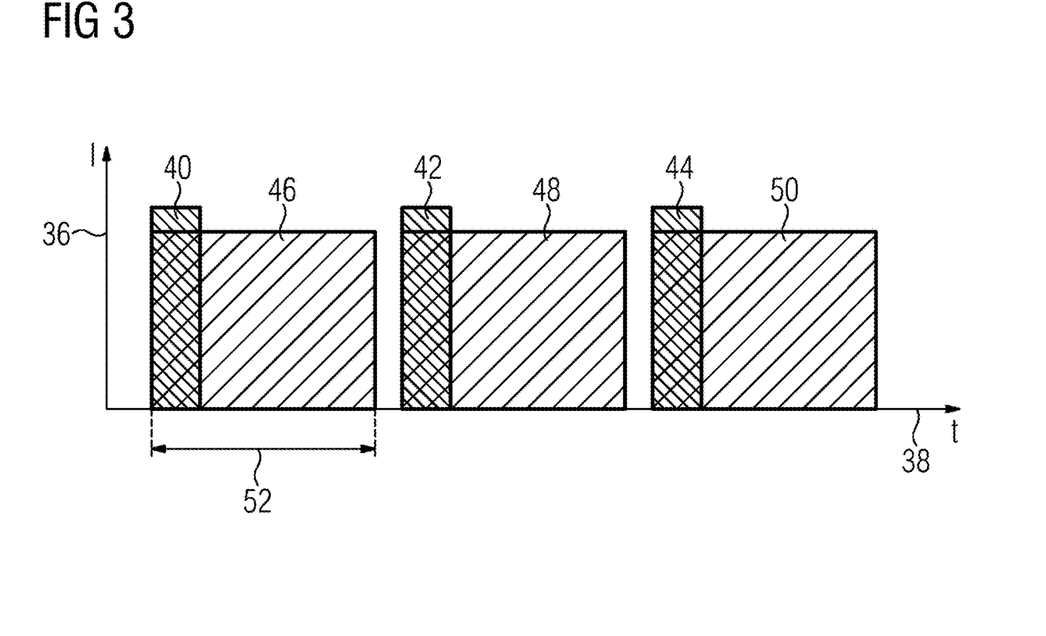
FIG. 3 shows a schematic diagram view of three successive exemplary x-ray pulses.

FIG. 3 shows a schematic diagram view in which the ordinate 36 indicates an intensity of the x-ray radiation emitted by the radiation source 10 and the time is plotted on the abscissa 38. For comparison purposes, three short consecutive x-ray pulses 40, 42, 44 corresponding to the prior art are shown. According to previous methods known from the prior art, no x-ray radiation is emitted between the short x-ray pulses 40 to 44 (e.g., the radiation source 10 is operated in pulsed mode). In this case, a duty cycle of 10% is typically employed in the prior art. In contrast thereto, three successive x-ray pulses 46, 48, 50 used or usable for the present method are also shown, which, compared to the short x-ray pulses 40 to 44, have a significantly longer pulse length or pulse duration 52. In this case, the radiation source 10 may be operated, for example, in pulsed mode at a duty cycle of 90%. However, a continuous mode of operation or a mode of operation having a duty cycle of 100% may also be provided. In the present example, the movement of the slit diaphragm 16 is coordinated with the pulse duration 52 and the duty cycle used such that the duration of the scan corresponds to the pulse duration 52 or to a time interval between respective start times of two successive pulses of the x-ray pulses 46 to 50.

Figure 4:
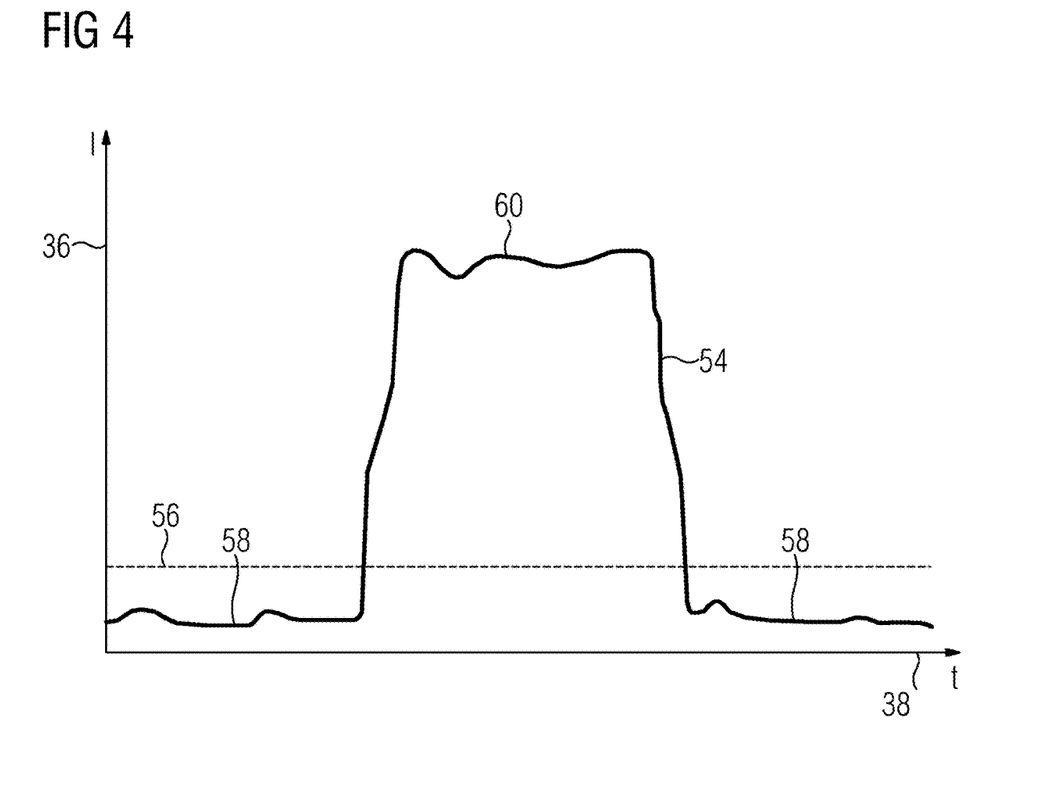
FIG. 4 shows a schematic diagram view of a variation with respect to time of an intensity curve of x-ray radiation at a detector pixel.

FIG. 4 shows a schematic diagram view in which the radiation intensity registered or detected by one of the pixels 22 is plotted on the ordinate 36 and the abscissa 38 indicates the time. Different scaling schemes are used in the views shown in FIGS. 3 and 4, and no direct comparison is possible or intended.

In the diagram shown in FIG. 4, there is illustrated in the present case an intensity curve 54 that represents by way of example a variation with respect to time of the radiation intensity detected by an individual pixel of the pixels 22 during a scan. A threshold value 56 is indicated therein, with intensity values lying below the threshold value 56 representing a scatter intensity 58 that is caused or produced without irradiation by primary radiation (e.g., simply by irradiation by scattered radiation). Intensity values lying above the threshold value 56 correspond to a primary intensity 60 that is produced or effected by an illumination or irradiation of the pixel by primary radiation. The threshold value 56 may be settable or set (e.g., dynamically).

The threshold value 56 may, for example, be a percentile of a histogram of the object 24 to be x-rayed or of an image or x-ray image representing the object 24 to be x-rayed or be determined from such a histogram or percentile. In this case, the percentile may be chosen as a function of a water value of the object to be x-rayed, since the scattered radiation intensity is dependent on the water value. The water value may be determined, for example, from a thickness or extension of the object 24 to be x-rayed in the irradiation direction. This is possible and useful, for example, in the case of organic objects to be x-rayed, such as human or animal patients, for example, since corresponding tissue has a significant water component and the water is relatively evenly distributed.

An increase in intensity from values lying below the threshold value 56 to the primary intensity 60 is clearly to be seen in the variation with respect to time of the intensity curve 54. This increase occurs when the bundle of rays 26 reaches the respective pixel during the scan. While the pixel is illuminated by the bundle of rays 26 (e.g., the primary radiation), the respective pixel detects the primary intensity 60. This or a characteristic curve substantially forms a plateau while the bundle of rays 26 traverses the pixel. As soon as the bundle of rays 26 no longer irradiates or illuminates the respective pixel in the course of the scan, the intensity detected by the pixel drops abruptly once again to values lying below the threshold value 56 (e.g., down to the scatter intensity 58).

Referring to FIGS. 1 to 4, two possible execution sequences of the present method are explained hereinbelow with reference to FIGS. 5 and 6.

Figure 5:
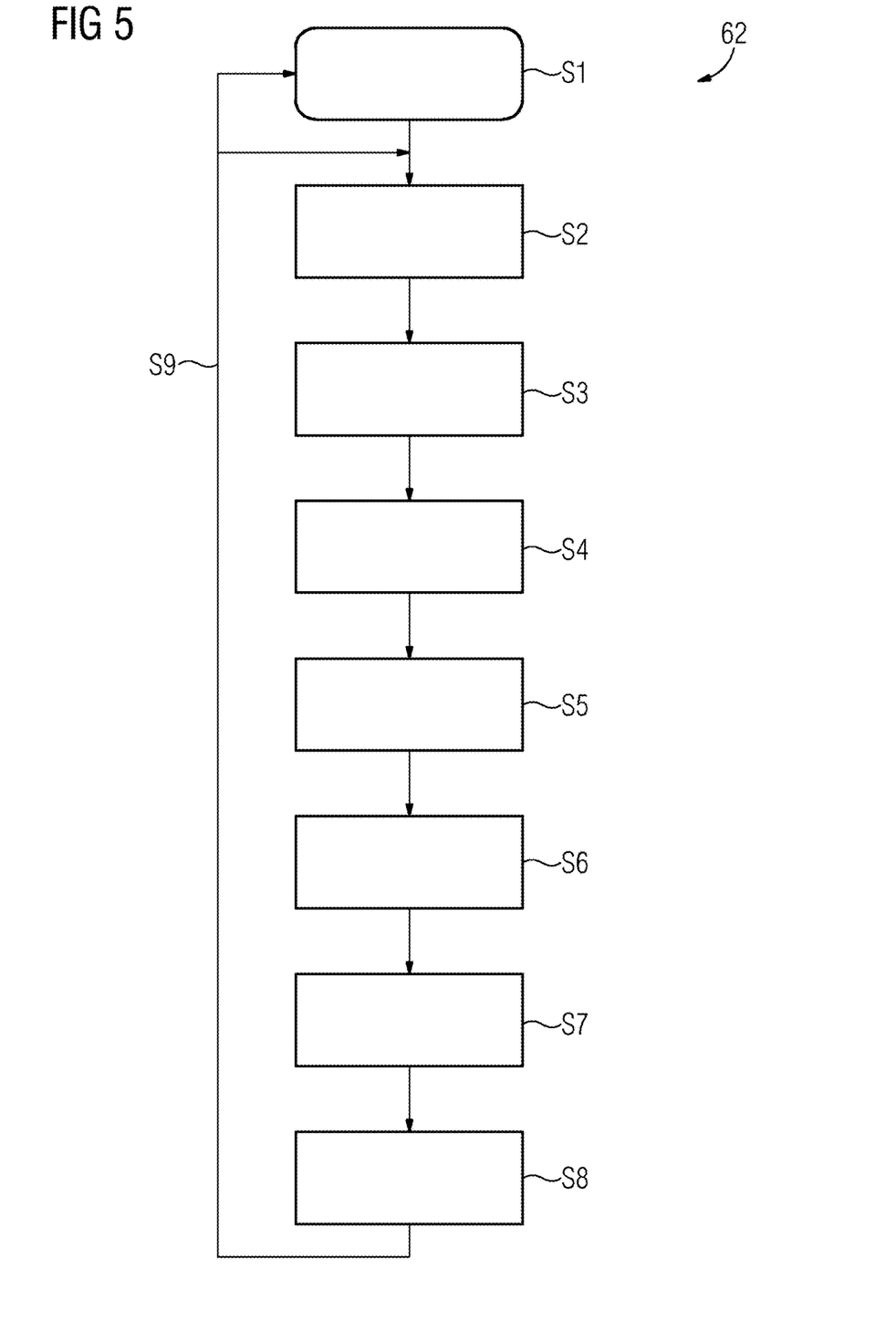
FIG. 5 shows a schematic flowchart of a method according to a first embodiment.

FIG. 5 shows a first schematic flowchart 62 of a method for generating x-ray images. The method is started in a method act S1. The radiation source 10 may be switched on or put into operation, and the movement of the slit diaphragm 16 (e.g., therefore, the scan of the object to be x-rayed) may be started. In order to provide a maximally uniform scanning movement, the slit diaphragm 16 may also be brought or accelerated to a predetermined constant rotational speed already before the radiation source 10 is switched on. The switch-on time of the radiation source 10 may then be synchronized accordingly to a current position or setting of the slit diaphragm 16 or the slit 18. In this way, the bundle of rays 26 is therefore moved over the object to be x-rayed.

During the scan, in a method act S2, a first constituent image dataset is read out from the detector 20 and forwarded, transmitted, or provided to a data processing device (not shown). After the first constituent image dataset has been read out completely, a second constituent image dataset is read out from the detector 20 in a following method act S3 and likewise provided to the data processing device. After the second constituent image dataset has also been read out completely, a third constituent image dataset is read out from the detector 20 in a following method act S4 and provided to the data processing device.

Method acts S2 to S4 are in this case performed during the scan of the object to be x-rayed started in method act S1. For that purpose, in the present example, the detector 20 may be read out at a rate or image readout rate of at least 60 Hz or 60 fps (frames per second or constituent image datasets per second). In this case, the three constituent image datasets may be read out in method acts S2 to S4 immediately after one another and/or limited only by the maximum image readout rate of the detector 20. However, a predefined period of time or time interval may be provided between method act S2 and method act S3 and method act S3 and method act S4, respectively. The period of time may be predefined, influenced, or dictated, for example, by a response time or a set integration time of the pixels 22 and/or by a size or width of the bundle of rays 26 and/or a speed of the bundle of rays 26 along the detector 20.

After or concurrently with method act S4, the scan of the object to be x-rayed started in method act S1 may be ended or stopped in a method act S5. If a moving average is used in the image processing, in one embodiment, no stop is performed at this point. The reading out of the three constituent image datasets in method acts S2 to S4 is provided as an example, and a different number of readout operations and constituent image datasets may also be provided during the scan. For example, six constituent image datasets may be provided or read out during a scan of 100 ms duration at an image readout rate of at least 60 Hz.

In a method act S6, a threshold value filter is applied to the individual constituent image datasets in order to discard image areas or data domains having a detected intensity or having intensity values below the threshold value 56. As a result, therefore, only those image areas and data domains or subdomains of the constituent image datasets corresponding to an irradiation by primary radiation remain. By this procedure, noise caused by scattered radiation may be effectively filtered out or removed from the image or intensity data registered by the detector 20.

In a method act S7, the remaining subdomains of the constituent image datasets filtered in this way are combined with one another in order to obtain an x-ray image or overall x-ray image of the object to be x-rayed. No intensity values corresponding only to a scattered radiation and detected by the respective dark pixels 32 are therefore contained in the overall x-ray image or final x-ray image. As a result of this, an improved image quality is achieved. The threshold value filter may be applied in each case immediately after the respective constituent image dataset has been read out.

In a method act S8, a reset may be performed. In this case, for example, the fully assembled overall x-ray image is output, and/or the constituent image datasets are stored in respective storage areas until the constituent image datasets are released. In this way, in a method act S9, a branch may be made in a kind of loop to a start of the method or, as the case may be, a new pass may be made through the method in order, for example, to generate or acquire a series of sequential x-ray images or overall x-ray images of the object to be x-rayed.

Figure 6:
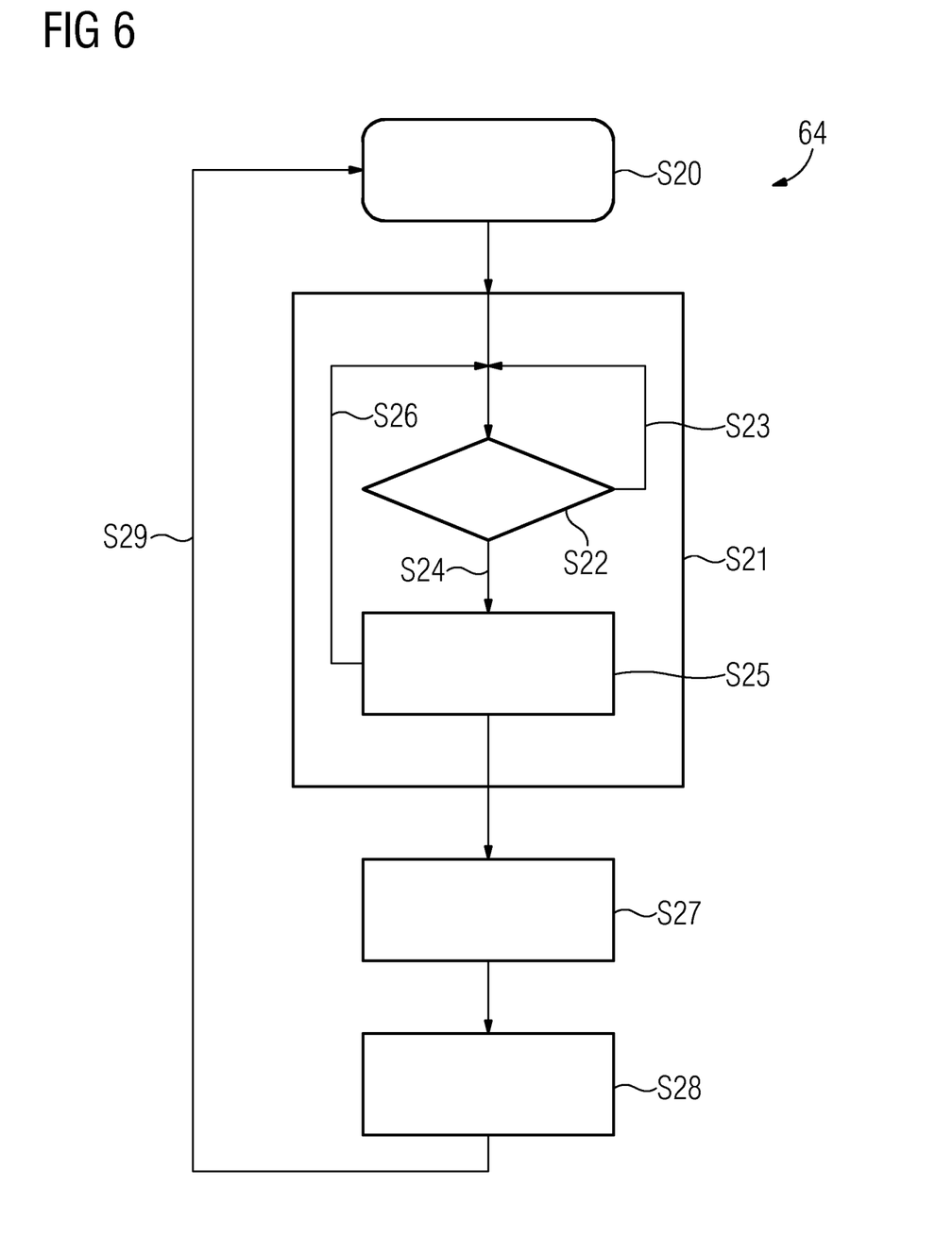
FIG. 6 shows a schematic flowchart of a method according to a second embodiment.

FIG. 6 shows an alternative schematic flowchart 64 of a method for generating x-ray images. In this case also, the method is first started in a method act S20, which, for example, may correspond to method act S1. Next, in a method act S21, a scan of the object to be x-rayed is performed. During the scan, a query takes place continuously in a method act S22 in each pixel 22 or for each of the pixels 22. By this query, it is checked whether a radiation intensity incident on the pixel at the respective time instant lies above or below the threshold value 56. The threshold value 56 is able to be set dynamically in this case also. If the incident radiation intensity is lower than the threshold value 56, then the query is repeated in a method act S23. This query loop serves merely schematically for illustration purposes and does not need to be realized, for example, as an actual logic circuit. Instead, for example, an analog, electrical, or electronic circuit or arrangement that responds only when the threshold value is reached may be provided.

If it is established at a specific time instant by the query that the incident radiation intensity is greater than the threshold value 56, then an integration of the incident radiation intensity is started in a method act S24. For that purpose, it may be provided that the pixels 22 are active pixels (e.g., that the detector 20 has an active pixel sensor). This enables the incident radiation intensity to be evaluated in a pixel-precise manner. While the integration is running, the query (e.g., the threshold value comparison of the incident radiation intensity) continues to be performed repeatedly in a method act S26. As soon as the incident radiation intensity becomes smaller or is less than the threshold value 56, the integration is stopped. Passes through this loop are performed continuously during the entire scan, with the result that the total radiation intensity impinging on the respective pixel and having instantaneous values above the threshold value 56 is integrated or added and the detected radiation intensities having instantaneous values below the threshold value 56 are ignored or discarded.

After the scan has ended, terminated, or stopped, the detector 20 is read out in a subsequent method act S27, with the result that all of the respective total integration values of the individual pixels 22 are therefore acquired. In this case, therefore, the detector 20 is read out only once per scan in order to obtain an overall x-ray image of the object to be x-rayed. The overall x-ray image is composed of the integrated intensity values of the individual pixels 22 and is provided in a following method act S28. At the same time, the integrators or integrator circuits of the individual pixels 22 are also reset so that the detector 20 and the x-ray system are primed in preparation for a fresh scan for generating or acquiring a further x-ray image. Accordingly, a return or branch may be made in a method act S29 to a starting point of the method in order to perform a new pass through the method for acquiring a next x-ray image.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating x-ray images, the method comprising:
   generating an x-ray image, the generating of the x-ray image comprising:
      moving a first slit diaphragm in front of an object to be x-rayed along a path extending between a radiation source and an object to be x-rayed for the purpose of scanning the object;
      detecting radiation emitted by the radiation source by a detector after the radiation has passed through the first slit diaphragm and the object to be x-rayed, wherein the x-ray image is generated without the use of a second slit diaphragm arranged between the object to be x-rayed and the detector; and
      evaluating only radiation detected during the scan by the detector having an intensity that is greater than a predefined threshold value,
   wherein the first slit diaphragm is rotatably mounted and during the scan, is rotated around an axis of rotation that extends at least approximately parallel to a central ray of a bundle of rays emitted by the radiation source.

2. The method of claim 1, wherein the generating of the x-ray image comprises:
   reading out a plurality of constituent image datasets from the detector during the scan; and
   assembling the x-ray image from all subdomains of the plurality of constituent image datasets in which the detected intensity is greater than the predefined threshold value.

3. The method of claim 2, wherein the plurality of constituent image datasets are read out from the detector at a rate of at least 60 hertz.

4. The method of claim 3, wherein the radiation source is operated in pulsed mode at a duty cycle of at least 50 percent.

5. The method of claim 3, wherein the radiation source is operated continuously during a successive generation of multiple x-ray images.

6. The method of claim 3, wherein the first slit diaphragm is rotatably mounted and during the scan, is rotated around an axis of rotation that extends at least approximately parallel to a central ray of a bundle of rays emitted by the radiation source.

7. The method of claim 1, wherein the detector has an active pixel sensor, and
   wherein the radiation detected by the active pixel sensor during the scan using the detector is ignored in a pixel-precise manner when the respective intensity is less than the threshold value, and is integrated in a pixel-precise manner when the respective intensity is greater than the threshold value.

8. The method of claim 1, wherein the radiation source is operated in pulsed mode at a duty cycle of at least 50 percent.

9. The method of claim 8, wherein the radiation source is operated in pulsed mode at a duty cycle of at least 90 percent.

10. The method of claim 1, wherein the radiation source is operated continuously during a successive generation of multiple x-ray images.

11. An x-ray system comprising:
   a radiation source;
   a first slit diaphragm that is movably mounted;
   a detector; and
   a data processor,
   wherein the x-ray system is configured to:
      generate an x-ray image, the generation of the x-ray image comprising:
         movement of the first slit diaphragm in front of an object to be x-rayed along a path extending between the radiation source and the object to be x-rayed for the purpose of scanning the object;
         detection, by the detector, of radiation emitted by the radiation source after the radiation has passed through the first slit diaphragm and the object to be x-rayed, wherein the x-ray image is generated without the use of a second slit diaphragm arranged between the object to be x-rayed and the detector; and evaluation, by the data processor, of only radiation detected during the scan by the detector having an intensity that is greater than a predefined threshold value, wherein the first slit diaphragm is configured as a disk that is mounted as rotatable around an axis of rotation and has at least one slit extending in a radial direction.

12. The x-ray system of claim 11, wherein each slit of the at least one slit of the disk has a greater extension in the radial direction than in a circumferential direction of the disk.

13. The x-ray system of claim 11, wherein the disk has more than one slit extending in the radial direction.

\* \* \* \* \*